US012678445B2

(12) United States Patent
Goswami et al.

(10) Patent No.: US 12,678,445 B2
(45) Date of Patent: Jul. 14, 2026

(54) METHODS FOR TREATING GLIOBLASTOMA

(71) Applicant: BOARD OF REGENTS, THE UNIVERSITY OF TEXAS SYSTEM, Austin, TX (US)

(72) Inventors: Sangeeta Goswami, Houston, TX (US); Padmanee Sharma, Houstion, TX (US); James Allison, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 832 days.

(21) Appl. No.: 17/998,350

(22) PCT Filed: May 11, 2021

(86) PCT No.: PCT/US2021/031750
§ 371 (c)(1),
(2) Date: Nov. 9, 2022

(87) PCT Pub. No.: WO2021/231405
PCT Pub. Date: Nov. 18, 2021

(65) Prior Publication Data
US 2023/0255978 A1     Aug. 17, 2023

Related U.S. Application Data

(60) Provisional application No. 63/023,775, filed on May 12, 2020.

(51) Int. Cl.
| | |
|---|---|
| *A61K 31/55* | (2006.01) |
| *A61K 39/395* | (2006.01) |
| *A61K 45/06* | (2006.01) |
| *A61P 25/00* | (2006.01) |
| *A61P 35/00* | (2006.01) |
| *C07K 16/28* | (2006.01) |
| *C07K 16/40* | (2006.01) |
| *C12N 15/113* | (2010.01) |

(52) U.S. Cl.
CPC .......... *A61K 31/55* (2013.01); *A61K 39/3955* (2013.01); *A61K 45/06* (2013.01); *A61P 25/00* (2018.01); *A61P 35/00* (2018.01); *C07K 16/2818* (2013.01); *C07K 16/40* (2013.01); *C12N 15/1137* (2013.01); *C12N 2310/11* (2013.01); *C12N 2310/14* (2013.01); *C12N 2310/531* (2013.01)

(58) Field of Classification Search
CPC .... A61K 31/55; A61K 39/3955; A61K 45/06; A61K 39/39541; A61K 39/39558; A61K 38/00; A61K 31/713; A61P 25/00; A61P 35/00; C07K 16/2818; C07K 16/40; C07K 16/2827; C07K 2317/76; C12N 15/1137; C12N 2310/11; C12N 2310/14; C12N 2310/531
See application file for complete search history.

(56) References Cited

U.S. PATENT DOCUMENTS

| | | | | |
|---|---|---|---|---|
| 7,408,028 B2 * | 8/2008 | Xiao | ....................... | A61P 25/28 530/328 |
| 8,003,595 B2 * | 8/2011 | Avrameas | .............. | A61K 47/64 530/402 |
| 2003/0118610 A1 * | 6/2003 | Stern | .................... | C07K 14/585 435/5 |
| 2008/0020990 A1 * | 1/2008 | Yano | ......................... | A61P 7/00 536/23.1 |
| 2008/0057066 A1 * | 3/2008 | Dixit | ............... | C07K 14/70575 435/7.1 |
| 2011/0008422 A1 * | 1/2011 | Dekel | .................. | A61K 9/1277 424/491 |
| 2012/0107337 A1 | 5/2012 | Lewandrowski et al. | | |
| 2013/0156694 A1 * | 6/2013 | Onikienko | ............. | C07K 16/46 424/1.49 |
| 2018/0140691 A1 | 5/2018 | Takasu et al. | | |
| 2018/0208990 A1 * | 7/2018 | Berthiaume | ......... | A61K 31/713 |
| 2019/0000831 A1 * | 1/2019 | Liau | ..................... | A61K 31/506 |
| 2019/0091229 A1 | 3/2019 | Lichenstein et al. | | |

FOREIGN PATENT DOCUMENTS

| | | | | |
|---|---|---|---|---|
| CN | 106999590 | 8/2017 | | |
| CN | 108884159 | 11/2018 | | |
| JP | 2017101011 | 6/2017 | | |
| JP | 6655820 | 2/2020 | | |
| WO | WO-2016005295 A1 * | 1/2016 | ............. | C07K 16/40 |
| WO | WO 2017/099829 | 6/2017 | | |

(Continued)

OTHER PUBLICATIONS

Rudikoff et al. Proceedings of the National Academy of Sciences USA, vol. 79, p. 1979-1983, 1982 (Year: 1982).*

(Continued)

*Primary Examiner* — Sean E Aeder
*Assistant Examiner* — Yie Chia Lee
(74) *Attorney, Agent, or Firm* — NORTON ROSE FULBRIGHT US LLP

(57) ABSTRACT

Aspects of the disclosure relate to a method of treating glioblastoma in a subject comprising administering to the subject a KDM6B inhibitor. In some aspects, the methods are performed in combination with an immunotherapy. Further aspects relate to a composition comprising a KDM6B inhibitor and an immunotherapy.

12 Claims, 9 Drawing Sheets

(56) References Cited

FOREIGN PATENT DOCUMENTS

WO      WO 2018/149986      8/2018
WO      WO 2021/127254      6/2021
WO      WO 2021/216620      10/2021

OTHER PUBLICATIONS

Evans et al. Q. J. Med 1999: 92: 299-307 (Year: 1992).*
Eck and Wilson. Goodman & Gilman's The Pharmacological basis of Therapeutics, 1996, McGraw-Hill, New York, NY. p. 77-101 ( Year: 1996).*
Verma and Somia. Nature, 1997, 389:239-242 (Year: 1997).*
Niidome and Huang. Gene Therapy, 2002, 9:1647-1652 (Year: 2002).*
Cuzick et al. The Lancet, vol. 361, p. 296-300, 2003 (Year: 2003).*
Parker et al. Expert Reviews in Molecular Medicine, 2003, 5:1-15 (Year: 2003).*
Komenaka et al. Clinics in Dermatology, 2004, vol. 22, p. 251-265 (Year: 2004).*
Schiffman et al. The New England Journal of Medicine, Vo. 353, No. 20, p. 2101-2104, 2005 (Year: 2005).*
Yamanaka et al. Expert Opinion on Biological Therapy, 7(5), 645-649, 2007 (Year: 2007).*
Jones et al. Pharmaceutical Research, vol. 24, No. 9, p. 1759-1771, 2007 (Year: 2007).*
Gao et al. The AAPS Journal, 2007, 9:E92-E104 (Year: 2007).*
Hernandez-Ledesma et al. Peptides, vol. 30, p. 426-430, 2009 (Year: 2009).*
McNaughton et al. Proceedings of the National Academy of Sciences, USA, vol. 106, No. 15, p. 6111-6116, 2009 (Year: 2009).*
Carter et al. Experimental Cell Research, vol. 317, p. 1261-1269, 2011 (Year: 2011).*
NCT01591356 (Record History May 2, 2012) (Year: 2012).*
Zhang et al. Molecular Therapy, 2012, 20:1298-1304 (Year: 2012).*
Hashizume et al. Nature Medicine vol. 20, pp. 1394-1396, 2014 (Year: 2014).*

Schulz-Knappe et al. Annals of the Rheumatic Diseases vol. 75, Supplement 2, Jun. 2016, pp. 275-276 (Year: 2016).*
Antonios et al. Neuro Oncol. Jan. 23, 2017;19(6):796-807 (Year: 2017).*
Filley et al. Oncotarget, 2017, vol. 8, (No. 53), pp. 91779-91794 (Year: 2017).*
International Search Report and Written Opinion in corresponding PCT Application No. PCT/US2021/031750, mailed Aug. 9, 2021.
Extended European Search Report issued in Corresponding European Application No. 21803272.0, dated May 8, 2024.
Hashizume et al., "Pharmacologic inhibition of histone demethylation as a therapy for pediatric brainstem glioma," Nature Medicine, Nov. 2014, vol. 20, No. 12, pp. 1394-1396.
Liau et al., "Adaptive Chromatin Remodeling Drives Glioblastoma Stem Cell Plasticity and Drug Tolerance," Cell Stem Cell, Dec. 2016, vol. 20, No. 2, pp. 233.
Romani et al., "Targeting of Histone Demethylases KDM5A and KDM6B Inhibits the Proliferation of Temozolomide-Resistant Glioblastoma Cells," Cancers, Jun. 2019, vol. 11, No. 6, pp. 878.
Sui et al., "The pharmacological role of histone demethylase JMJD3 inhibitor GSK-J4 on glioma cells," Oncotarget, Sep. 2017, vol. 8, No. 40, pp. 68591-68598.
Brown et al., "Regression of Glioblastoma after Chimeric Antigen Receptor T-Cell Therapy," Ne J Med, Dec. 29, 2016; vol. 375, No. 26, pp. 2561-2569.
Goswami et al., "Myeloid-specific KDM6B inhibition sensitizes glioblastoma to PD1 blockade," Nat Cancer, Oct. 2023, vol. 4, pp. 1455-1473.
Jinushi et al., "The impact of molecular therapy on tumor immunity," The Japanese Journal of Clinical Medicine (Nipponrinsho), 2015, vol. 73, No. 8, pp. 1349-1354.
Shao et al., Tumor of the Breast, Shanghai, Fudan University Press, Sep. 30, 2018, pp. 89-92. (Translation not available at this time.).
Terasaki et al., "Vaccination therapy," The Japanese Journal of Clinical Medicine (Nipponrinsho), 2015, vol. 74, Suppl. 7, pp. 769-775. (Translation not available at this time.).

* cited by examiner

METHODS FOR TREATING GLIOBLASTOMA

This application is a national phase application under 35 U.S.C. § 371 of International Application No. PCT/US2021/031750, filed May 11, 2021, which claims benefit of priority of U.S. Provisional Application No. 63/023,775, filed May 12, 2020, both of which are hereby incorporated by reference in their entirety.

BACKGROUND OF THE INVENTION

I. Field of the Invention

This invention relates to the field of biotechnology and therapeutic treatment methods.

II. Background

Tremendous advances were made in cancer therapy in the past decade through the use of targeted therapy and immune therapy. By blocking immune inhibitory ligand-receptor interactions involving CTLA-4 and PD-1, checkpoint blockade immunotherapy relieves T lymphocytes of major inhibitory signals, thus potentiating underlying T cell-mediated anti-tumor immune activity. However, ubiquitous relief of inhibitory signals systemically can also activate T lymphocytes reactive against self-antigens, leading to loss of self-tolerance and immune-related adverse events. Patients who develop high-grade toxicities commonly require either temporary or permanent discontinuation of treatment, and may require prolonged periods of heavy immunosuppression in order to manage their toxicities. The high frequency of developing severe to life threatening toxicity to anti-CTLA-4 and/or anti-PD-1 therapy and the unpredictability with respect to whether a patient will respond has become a limiting factor for clinicians to prescribe this form of therapy.

While some factors associated with patient response to immune checkpoint inhibitor therapy have been discovered, there is a need for predictors of toxicity due to immune checkpoint blockade therapy and predictors of responders to immune checkpoint blockade therapy. Stratifying patients into those that are likely and unlikely to respond to checkpoint blockade therapy, based on one or more biomarkers, will provide for more effective and therapeutic treatment methods for patients, because patients can be provided with the most effective therapy before further spreading of the disease.

SUMMARY OF THE INVENTION

Aspects of the disclosure relate to methods of treating glioblastoma in a subject comprising administering to the subject a KDM6B inhibitor. Further aspects relate to compositions comprising a KDM6B inhibitor and an immunotherapy. Further aspects relate to a method for reducing a glioblastoma tumor size or volume in a subject comprising administering to the subject a KDM6B inhibitor. Aspects of the disclosure also relate to killing glioblastoma cancer cells comprising administering a KDM6B inhibitor to the cells. Also described are method for increasing overall survival, reducing rate of recurrence, and/or increasing recurrence free survival in a subject having glioblastoma, the method comprising administering to the subject a KDM6B inhibitor. The glioblastoma may comprise primary or secondary glioblastoma. Gliblastoma may refer to glioblastoma multiforme and/or brain cancer. The subject may be one that has been diagnosed with glioblastoma. The glioblastoma may be further defined as glioblastoma with myeloid infiltration. The term myeloid infiltration refers to a glioblastoma that has myeloid cells present in the tumor microenvironment. In some aspects, the subject has been determined to have myeloid infiltration.

In some aspects. KDM6B is inhibited ex vivo in myeloid cells. For example, bone marrow cells may be isolated from the subject or from a bone marrow donor subject. The cells may be cultured in medium and/or conditions that allow for the growth of macrophages. The cells can then be contacted with the KDM6B inhibitor. The cells may then be administered to the patient.

In some aspects, KDM6B is inhibited in myeloid cells. The method may further comprises administration of an immunotherapy. The immunotherapy may be administered before the KDM6B inhibitor, after the KDM6B inhibitor, or at the same time as the KDM6B inhibitor. In some aspects the immunotherapy is administered after the inhibitor of KDM6B. In some aspects, the immunotherapy comprises immune checkpoint blockade (ICB) therapy. The ICB therapy may be a monotherapy or a combination ICB therapy. The ICB therapy may comprise an inhibitor of PD-1, PDL1, PDL2, CTLA-4, B7-1, and/or B7-2. In some aspects, the ICB therapy comprises an anti-PD-1 monoclonal antibody and/or an anti-CTLA-4 monoclonal antibody. In some aspects, the ICB therapy comprises one or more of nivolumab, pembrolizumab, pidilizumab, ipilimumab, and tremelimumab.

In some aspects, the subject has previously treated for glioblastoma with an anticancer agent. In some aspects, the previous treatment comprises an immunotherapy. In some aspects, the subject has been determined to be non-responsive to the previous therapy. In some aspects, the method further comprises administering at least one additional anticancer treatment. In some aspects, the at least one additional anticancer treatment is surgical therapy, chemotherapy, radiation therapy, hormonal therapy, immunotherapy, small molecule therapy, receptor kinase inhibitor therapy, anti-angiogenic therapy, cytokine therapy, cryotherapy or a biological therapy.

In some aspects, the glioblastoma comprises stage I, II, III, or IV glioblastoma. In some aspects, the glioblastoma comprises recurrent and/or metastatic glioblastoma. The therapeutic agent of the disclosure, such as the KDM6B inhibitor, immunotherapy, and/or additional anticancer agent may be administered orally, intravenously, intraperitoneally, intratracheally, intratumorally, intramuscularly, endoscopically, intralesionally, percutaneously, subcutaneously, regionally, or by direct injection or perfusion. In some aspects, the KDM6B inhibitor, immunotherapy, and/or additional anticancer agent is administered intravenously. In some aspects, the KDM6B inhibitor, immunotherapy, and/or additional anticancer agent is administered more than once.

The inhibitor may be a small molecule compound. In some aspects, the inhibitor comprises GSK J4. The inhibitor may be an isolated nucleic acid molecule that hybridizes with a nucleic acid molecule encoding KDM6B. The inhibitor may be a nucleic acid inhibitor that inhibits transcription or translation of a KDM6B nucleic acid. In some aspects, the inhibitor is an siRNA, a double stranded RNA, a short hairpin RNA, or an antisense oligonucleotide. In some aspects, the inhibitor is siRNA. In some aspects, the inhibitor is an antibody that binds to a KDM6B protein and inhibits the activity of KDM6B.

The inhibitor may be administered systemically. In some aspects, the inhibitor is administered intra-tumorally or to the tumor microenvironment. In some aspects, the inhibitor is administered to a subject having a gliblastoma tumor. In some aspects, administration of the inhibitor significantly reduces the volume of the tumor. In some aspects, administration of the inhibitor extends the survival of the subject. In some aspects, administration of the inhibitor increases overall survival or recurrence free survival in the subject.

The subject may be a human, mouse, pig, cow, sheep, rabbit, or rat. In some aspects, the subject is a non-human primate. In some aspects, the subject is a human or a mammal.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone. "z" alone, "x, y, and z," "(x and y) or z," "x or (y and z)," or "x or y or z." It is specifically contemplated that x, y, or z may be specifically excluded from an embodiment.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

Use of the one or more sequences or compositions may be employed based on any of the methods described herein. Other embodiments are discussed throughout this application. Any embodiment discussed with respect to one aspect of the disclosure applies to other aspects of the disclosure as well and vice versa.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

I. KDM6B Inhibitors

Figure 1:
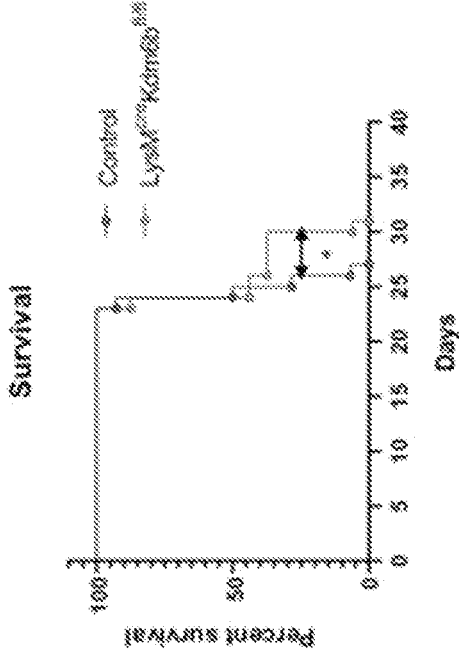
FIG. 1 shows myeloid specific depletion of KDM6B reduce tumor volume and improve survival of GBM tumor bearing mice.
Figure 1:
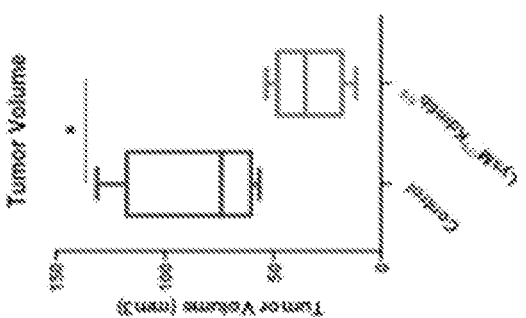
Figure 1:
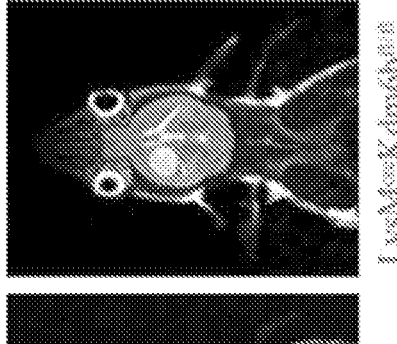
Figure 1:
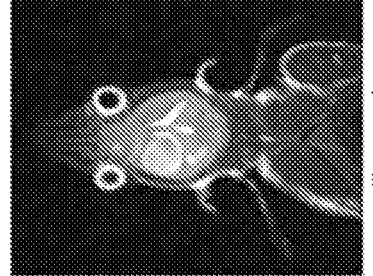

A KDM6B inhibitor may refer to any member of the class of compound or agents having an IC50 of 100 μM or lower concentration for a KDM6B activity, for example, at least or at most or about 200, 100, 80, 50, 40, 20, 10, 5, 1 μM, 100, 10, 1 nM or lower concentration (or any range or value derivable therefrom) or any compound or agent that inhibits the expression of KDM6B. Examples of KDM6B activity or function may include, but not be limited to, the regulation of Na+/H+ levels in cells, intracellular pH, secretion of ions into medium apoptosis, cell proliferation, cell cycle, cell death, or cell viability. In particular aspects, the regulation can be an increase or decrease as compared with a control level or sample. In further aspects, functional assay such as intra cellular pH calculation, acid loading test to culture media, crystal analysis of KDM6B, electron microscope may be used. In additional aspects, MTT assay, colony formation assay, invasion assay, apoptosis assay, or cell cycle analysis may be used to test the KDM6B inhibitors.

A. KDM6B Inhibitory Nucleic Acids

Inhibitory nucleic acids or any ways of inhibiting gene expression of KDM6B known in the art are contemplated in certain aspects. Examples of an inhibitory nucleic acid include but are not limited to siRNA (small interfering RNA), short hairpin RNA (shRNA), double-stranded RNA, an antisense oligonucleotide, a ribozyme and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain aspects from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein. "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Particularly, an inhibitory nucleic acid may be capable of decreasing the expression of KDM6B by at least 10%, 20%, 30%, or 40%, more particularly by at least 50%, 60%, or 70%, and most particularly by at least 75%, 80%, 90%, 95% or more or any range or value in between the foregoing.

In further aspects, there are synthetic nucleic acids that are KDM6B inhibitors. An inhibitor may be between 17 to 25 nucleotides in length and comprises a 5' to 3' sequence that is at least 90% complementary to the 5' to 3' sequence of a mature KDM6B mRNA. In certain aspects, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature KDM6B mRNA, particularly a mature, naturally occurring mRNA. In some embodiments, the nucleic acid is complementary to the 5' or 3' untranslated region of the KDM6B gene. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

In some aspects, the inhibitor nucleic acid may be a nucleic acid that alters the genome of the cell, such as through gene editing. For example, cells from the subject or donor subject may be subjected to gene editing to alter the genomic sequence of KDM6B in the cells through the use of techniques such as CRISPR/Cas9 or zinc fingers to modify the DNA. The cells may then be administered to the patient with the altered genetic sequence of KDM6B that reduces or eliminates expression of the gene.

B. KDM6B Inhibitory Antibodies

In certain aspects, an antibody or a fragment thereof that binds to at least a portion of KDM6B protein and inhibits KDM6B activity in histone demethylation; its associated use in treatment of diseases is contemplated in aspects.

In some aspects, the anti-KDM6B antibody is a monoclonal antibody or a polyclonal antibody. In some aspects, the antibody is a chimeric antibody, an affinity matured antibody, a humanized antibody, or a human antibody. In some aspects, the antibody is an antibody fragment. In some aspects, the antibody is a Fab, Fab', Fab'-SH, F(ab')2, or scFv. In one aspect, the antibody is a chimeric antibody, for example, an antibody comprising antigen binding sequences from a non-human donor grafted to a heterologous non-human, human or humanized sequence (e.g., framework and/or constant domain sequences). In one aspect, the non-human donor is a mouse. In one aspect, an antigen binding sequence is synthetic, e.g., obtained by mutagenesis (e.g., phage display screening, etc.). In one aspect, a chimeric antibody has murine V regions and human C region. In one aspect, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VII domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VII domain and a VL domain are linked by a peptide linker which allows the two domains to associate to form a binding domain: (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with a KDM6B antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g. mouse) hybridoma cell line.

Methods have been developed to replace light and heavy chain constant domains of the monoclonal antibody with analogous domains of human origin, leaving the variable regions of the foreign antibody intact. Alternatively. "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091, 513, and 6,881,557, which are incorporated herein by this reference.

By known means as described herein, polyclonal or monoclonal antibodies, binding fragments and binding domains and CDRs (including engineered forms of any of the foregoing), may be created that are specific to KDM6B protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939.350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to KDM6B will have the ability to neutralize or counteract the effects of the KDM6B regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

C. KDM6B Inhibitory Small Molecules

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain aspects, small molecules are less than about 1000 grams/mole. In certain aspects, small molecules are less than about 550 grams/mole. In certain aspects, small molecules are between about 200 and about 550 grams/mole. In certain aspects, small molecules exclude peptides (e.g., compounds comprising 2 or more amino acids joined by a peptidyl bond). In certain aspects, small molecules exclude nucleic acids.

For example, a small molecule KDM6B inhibitory may be any small molecules that is determined to inhibit KDM6B function or activity. Such small molecules may be determined based on functional assays in vitro or in vivo.

I. Immunotherapy

In some aspects, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumour-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies are known in the art, and some are described below.

A. Immune Checkpoint Blockade Therapy

Aspects of the disclosure may include administration of immune checkpoint blockade therapy, which are further described below.

1. PD-1, PDL1, and PDL2 Inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PDL1 on epithelial cells and tumor cells. PDL2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PDL1 activity.

Alternative names for "PD-1" include CD279 and SLEB2. Alternative names for "PDL1" include B7-1, B7-4, CD274, and B7-H. Alternative names for "PDL2" include B7-DC, Btdc, and CD273. In some aspects, PD-1, PDL1, and PDL2 are human PD-1, PDL1 and PDL2.

In some aspects, the PD-1 inhibitor is a molecule that inhibits the binding of PD-1 to its ligand binding partners. In a specific aspect, the PD-1 ligand binding partners are PDL1 and/or PDL2. In another aspect, a PDL1 inhibitor is a molecule that inhibits the binding of PDL1 to its binding partners. In a specific aspect, PDL1 binding partners are PD-1 and/or B7-1. In another aspect, the PDL2 inhibitor is a molecule that inhibits the binding of PDL2 to its binding partners. In a specific aspect, a PDL2 binding partner is PD-1. The inhibitor may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some aspects, the PD-1 inhibitor is an anti-PD-1 antibody (e.g., a human antibody, a humanized antibody, or a chimeric antibody). In some aspects, the anti-PD-1 antibody is selected from the group consisting of nivolumab, pembrolizumab, and pidilizumab. In some aspects, the PD-1 inhibitor is an immunoadhesin (e.g., an immunoadhesin comprising an extracellular or PD-1 binding portion of PDL1 or PDL2 fused to a constant region (e.g., an Fc region of an immunoglobulin sequence). In some aspects, the PDL1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 inhibitors include MEDI0680, also known as AMP-514, and REGN2810.

In some aspects, the ICB therapy comprises a PDL1 inhibitor such as Durvalumab, also known as MEDI4736, atezolizumab, also known as MPDL3280A, avelumab, also known as MSB00010118C, MDX-1105. BMS-936559, or combinations thereof. In certain aspects, the ICB therapy comprises a PDL2 inhibitor such as rHIgM12B7.

In some aspects, the inhibitor comprises the heavy and light chain CDRs or VRs of nivolumab, pembrolizumab, or pidilizumab. Accordingly, in one aspect, the inhibitor comprises the CDR1, CDR2, and CDR3 domains of the VII region of nivolumab, pembrolizumab, or pidilizumab, and the CDR1, CDR2 and CDR3 domains of the VL region of nivolumab, pembrolizumab, or pidilizumab. In another aspect, the antibody competes for binding with and/or binds to the same epitope on PD-1, PDL1, or PDL2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

2. CTLA-4, B7-1, and B7-2

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4. B7-1, and/or B7-2 activity. In some aspects, the inhibitor blocks the CTLA-4 and B7-1 interaction. In some aspects, the inhibitor blocks the C71LA-4 and B7-2 interaction.

In some aspects, the ICB therapy comprises an anti-CTIA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VII and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab: formerly ticilimumab), U.S. Pat. No. 6,207,156; Hurwitz et al., 1998: can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as an ICB therapy in the methods and compositions of the disclosure is ipilimumab (also known as 10D1, MDX-010, MDX-101, and Yervoy®) or antigen binding fragments and variants thereof (see, e.g., WO0 1/14424).

In some aspects, the inhibitor comprises the heavy and light chain CDRs or VRs of tremelimumab or ipilimumab. Accordingly, in one aspect, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another aspect, the antibody competes for binding with and/or binds to the same epitope on PD-1, B7-1, or B7-2 as the above-mentioned antibodies. In another aspect, the antibody has at least about 70, 75, 80, 85, 90, 95, 97, or 99% (or any derivable range therein) variable region amino acid sequence identity with the above-mentioned antibodies.

B. Inhibition of Co-Stimulatory Molecules

In some aspects, the immunotherapy comprises an inhibitor of a co-stimulatory molecule. In some aspects, the inhibitor comprises an inhibitor of B7-1 (CD80), B7-2

(CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

C. Dendritic cell therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor. Dendritic cell receptors such as TLR3, TLR7, TLR8 or CD40 have been used as antibody targets.

D. CAR-T Cell Therapy

Chimeric antigen receptors (CARs, also known as chimeric immunoreceptors, chimeric T cell receptors or artificial T cell receptors) are engineered receptors that combine a new specificity with an immune cell to target cancer cells. Typically, these receptors graft the specificity of a monoclonal antibody onto a T cell. The receptors are called chimeric because they are fused of parts from different sources. CAR-T cell therapy refers to a treatment that uses such transformed cells for cancer therapy.

The basic principle of CAR-T cell design involves recombinant receptors that combine antigen-binding and T-cell activating functions. The general premise of CAR-T cells is to artificially generate T-cells targeted to markers found on cancer cells. Scientists can remove T-cells from a person, genetically alter them, and put them back into the patient for them to attack the cancer cells. Once the T cell has been engineered to become a CAR-T cell, it acts as a "living drug". CAR-T cells create a link between an extracellular ligand recognition domain to an intracellular signalling molecule which in turn activates T cells. The extracellular ligand recognition domain is usually a single-chain variable fragment (scFv). An important aspect of the safety of CAR-T cell therapy is how to ensure that only cancerous tumor cells are targeted, and not normal cells. The specificity of CAR-T cells is determined by the choice of molecule that is targeted.

Exemplary CAR-T therapies include Tisagenlecleucel (KYMRIAH®) and Axicabtagene ciloleucel (YES-CARTA®). In some aspects, the CAR-T therapy targets CD19.

E. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFNα and IFNβ), type II (IFNγ) and type III (IFNλ).

Interleukins have an array of immune system effects. IL-2 is an exemplary interleukin cytokine therapy.

F. Adoptive Cell Therapy

Adoptive cell therapy is a form of passive immunization by the transfusion of cells (adoptive cell transfer), such as T cells, macrophages, or myeloid cells. They are found in blood and tissue and usually activate when they find foreign pathogens. Specifically they activate when the cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumour death.

Multiple ways of producing and obtaining tumour targeted immune cells have been developed. T-cells specific to a tumor antigen can be removed from a tumor sample (TILs) or filtered from blood. Subsequent activation and culturing is performed ex vivo, with the results reinfused. Activation can take place through gene therapy, or by exposing the T cells to tumor antigens.

It is contemplated that a cancer treatment may exclude any of the cancer treatments described herein. Furthermore, aspects of the disclosure include patients that have been previously treated for a therapy described herein, are currently being treated for a therapy described herein, or have not been treated for a therapy described herein. In some aspects, the patient is one that has been determined to be resistant to a therapy described herein. In some aspects, the patient is one that has been determined to be sensitive to a therapy described herein.

II. Additional Therapies

The current methods and compositions of the disclosure may include one or more additional therapies known in the art and/or described herein. In some aspects, the additional therapy comprises an additional cancer treatment. In some aspects, the subject is one that has been treated with an additional therapy provided herein. In some aspects, the subject has been determined to be resistant to the additional therapy. Examples of such treatments are described herein, such as the immunotherapies described herein or the additional therapy types described in the following.

A. Oncolytic Virus

In some aspects, the additional therapy comprises an oncolytic virus. An oncolytic virus is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune responses for long-term immunotherapy B. Polysaccharides In some aspects, the additional therapy comprises polysaccharides. Certain compounds found in mushrooms, primarily polysaccharides, can up-regulate the immune system and may have anti-cancer properties. For example, beta-glucans such as lentinan have been shown in laboratory studies to stimulate macrophage. NK cells, T cells and immune system cytokines and have been investigated in clinical trials as immunologic adjuvants.

C. Neoantigens

In some aspects, the additional therapy comprises neoantigen administration. Many tumors express mutations. These mutations potentially create new targetable antigens (neoantigens) for use in T cell immunotherapy. The presence of CD8+ T cells in cancer lesions, as identified using RNA sequencing data, is higher in tumors with a high mutational burden. The level of transcripts associated with cytolytic activity of natural killer cells and T cells positively correlates with mutational load in many human tumors.

D. Chemotherapies

In some aspects, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dacarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as *vinca* alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-α), and (d) Miscellaneous Agents, such as platinum coordination complexes (e.g., cisplatin, carboplatin), substituted ureas (e.g., hydroxyurea), methyl-hydrazine derivatives (e.g., procarbazine), and adrenocortical suppressants (e.g., taxol and mitotane). In some aspects, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain aspects. In some aspects, the amount of cisplatin delivered to the cell and/or subject in conjunction with the construct comprising an Egr-1 promoter operably linked to a polynucleotide encoding the therapeutic polypeptide is less than the amount that would be delivered when using cisplatin alone.

Other suitable chemotherapeutic agents include antimicrotubule agents, e.g., Paclitaxel (TAXOL®) and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain aspects, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluorouracil; 5-FU) and floxuridine (fluorode-oxyuridine; FUDR®). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable aspect, the chemotherapeutic agent may be administered in an amount effective to cause arrest or regression of the cancer in a host, when the chemotherapy is administered with the construct. In other aspects, the chemotherapeutic agent may be administered in an amount that is anywhere between 2- to 10,000-fold less than the chemotherapeutic effective dose of the chemotherapeutic agent. For example, the chemotherapeutic agent may be administered in an amount that is about 20-fold less, about 500-fold less or even about 5000-fold less than the effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

E. Radiotherapy

In some aspects, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some aspects, the amount of ionizing radiation is greater than 20 Grays (Gy) and is administered in one dose. In some aspects, the amount of ionizing radiation is 18 Gy and is administered in three doses. In some aspects, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some aspects, the ionizing radiation is adminis- tered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some aspects, the amount of IR may be presented as a total dose of IR, which is then administered in fractionated doses. For example, in some aspects, the total dose is 50 Gy administered in 10 fractionated doses of 5 Gy each. In some aspects, the total dose is 50-90 Gy, administered in 20-60 fractionated doses of 2-3 Gy each. In some aspects, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some aspects, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein. In some aspects, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein), In some aspects, at least, at most, or exactly 1, 2, 3, 4, 5, 6, 7, 8, 9, 10, 11, or 12 (or any derivable range therein) fractionated doses are administered per day. In some aspects, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week, F. Surgery Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present aspects, chemotherapy, radio- therapy, hormonal therapy, gene therapy, immunotherapy, and/or alternative therapies. Tumor resection refers to physi- cal removal of at least part of a tumor. In addition to tumor resection, treatment by surgery includes laser surgery, cryo- surgery, electrosurgery, and microscopically-controlled sur- gery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1,2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Other Agents

It is contemplated that other agents may be used in combination with certain aspects of the present aspects to improve the therapeutic efficacy of treatment. These addi- tional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other aspects, cytostatic or differentiation agents can be used in combination with certain aspects of the present aspects to improve the anti-hyperproliferative efficacy of the treat- ments. Inhibitors of cell adhesion are contemplated to improve the efficacy of the present aspects. Examples of cell adhesion inhibitors are focal adhesion kinase (FAKs) inhibi- tors and Lovastatin. It is further contemplated that other agents that increase the sensitivity of a hyperproliferative cell to apoptosis, such as the antibody c225, could be used in combination with certain aspects of the present aspects to improve the treatment efficacy.

III. Cancer Monitoring

In certain aspects, the methods of the disclosure may be combined with one or more other cancer diagnosis or screening tests at increased frequency if the patient is determined to be at high risk for recurrence or have a poor prognosis based on the biomarker expression described above, such as expression level and/or presence of CD73 positive macrophages in a biological sample from the sub- ject.

In some aspects, the methods of the disclosure further include one or more monitoring tests. The monitoring pro- tocol may include any methods known in the art. In par- ticular, the monitoring include obtaining a sample and testing the sample for diagnosis. For example, the monitor- ing may include endoscopy, biopsy, endoscopic ultrasound, X-ray, barium swallow, a Ct scan, a MRI, a PET scan, laparoscopy, or biomarker testing. In some aspects, the monitoring test comprises radiographic imaging. Examples of radiographic imaging this is useful in the methods of the disclosure includes hepatic ultrasound, computed tomo- graphic (CT) abdominal scan, liver magnetic resonance imaging (MRI), body CT scan, and body MRI.

IV. Administration of Therapeutic Compositions

The therapy provided herein may comprise administration of a combination of therapeutic agents, such as a first cancer therapy and a second cancer therapy. In some aspects, the first cancer therapy comprises a KDM6B inhibitor and the second cancer therapy comprises an immunotherapy. In some aspects, the second cancer therapy comprises ICB therapy. The therapies may be administered in any suitable manner known in the art. For example, the first and second cancer treatment may be administered sequentially (at different times) or concurrently (at the same time). In some aspects, the first and second cancer treatments are administered in a separate composition. In some aspects, the first and second cancer treatments are in the same composition.

Aspects of the disclosure relate to compositions and methods comprising therapeutic compositions. The different therapies may be administered in one composition or in more than one composition, such as 2 compositions, 3 compositions, or 4 compositions. Various combinations of the agents may be employed.

The therapeutic agents of the disclosure may be administered by the same route of administration or by different routes of administration. In some aspects, the cancer therapy is administered intravenously, intramuscularly, subcutaneously, topically, orally, transdermally, intraperitoneally, intraorbitally, by implantation, by inhalation, intrathecally, intraventricularly, or intranasally. In some aspects, the antibiotic is administered intravenously, intramuscularly, subcutaneously, topically, orally, transdermally, intraperitoneally, intraorbitally, by implantation, by inhalation, intrathecally, intraventricularly, or intranasally. The appropriate dosage may be determined based on the type of disease to be treated, severity and course of the disease, the clinical condition of the individual, the individual's clinical history and response to the treatment, and the discretion of the attending physician.

The treatments may include various "unit doses." Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some aspects, a unit dose comprises a single administrable dose.

The quantity to be administered, both according to number of treatments and unit dose, depends on the treatment effect desired. An effective dose is understood to refer to an amount necessary to achieve a particular effect. In the practice in certain aspects, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 μg/kg, mg/kg, μg/day, or mg/day or any range derivable therein. Furthermore, such doses can be administered at multiple times during a day, and/or on multiple days, weeks, or months.

In certain aspects, the effective dose of the pharmaceutical composition is one which can provide a blood level of about 1 μM to 150 μM. In another aspect, the effective dose provides a blood level of about 4 μM to 100 μM; or about 1 μM to 100 μM; or about 1 μM to 50 μM; or about 1 μM to 40 μM; or about 1 μM to 30 μM; or about 1 μM to 20 PM; or about 1 μM to 10 μM; or about 10 μM to 150 μM; or about 10 μM to 100 μM; or about 10 μM to 50 μM: or about 25 μM to 150 μM: or about 25 μM to 100 μM; or about 25 μM to 50 μM; or about 50 μM to 150 μM; or about 50 μM to 100

μM (or any range derivable therein). In other aspects, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain aspects, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

V. Methods of Treatment

Provided herein are methods for treating or delaying progression of cancer in an subject through the administration of therapeutic compositions.

In some aspects, the therapies result in a sustained response in the individual after cessation of the treatment. The methods described herein may find use in treating conditions where enhanced immunogenicity is desired such as increasing tumor immunogenicity for the treatment of cancer.

In some aspects, the individual has cancer that is resistant (has been demonstrated to be resistant) to one or more anti-cancer therapies. In some aspects, resistance to anti-cancer therapy includes recurrence of cancer or refractory cancer. Recurrence may refer to the reappearance of cancer, in the original site or a new site, after treatment. In some aspects, resistance to anti-cancer therapy includes progression of the cancer during treatment with the anti-cancer therapy. In some aspects, the cancer is at early stage or at late stage.

In some aspects of the methods of the present disclosure, the cancer has low levels of T cell infiltration. In some aspects, the cancer has no detectable T cell infiltrate. In some aspects, the cancer is a non-immunogenic cancer (e.g., non-immunogenic colorectal cancer and/or ovarian cancer). Without being bound by theory, the combination treatment may increase T cell (e.g., CD4+ T cell, CD8+ T cell, memory T cell) priming, activation, proliferation, and/or infiltration relative to prior to the administration of the combination. The cancer may be a solid tumor, metastatic cancer, or non-metastatic cancer.

Methods may involve the determination, administration, or selection of an appropriate cancer "management regimen" and predicting the outcome of the same. As used herein the phrase "management regimen" refers to a management plan that specifies the type of examination, screening, diagnosis, surveillance, care, and treatment (such as dosage, schedule and/or duration of a treatment) provided to a subject in need thereof (e.g., a subject diagnosed with cancer).

The term "treatment" or "treating" means any treatment of a disease in a mammal, including: (i) preventing the disease, that is, causing the clinical symptoms of the disease not to develop by administration of a protective composition prior to the induction of the disease; (ii) suppressing the disease, that is, causing the clinical symptoms of the disease not to develop by administration of a protective composition after the inductive event but prior to the clinical appearance or reappearance of the disease; (iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance. In some aspects, the treatment may exclude prevention of the disease.

In certain aspects, further cancer or metastasis examination or screening, or further diagnosis such as contrast enhanced computed tomography (CT), positron emission tomography-CT (PET-CT), and magnetic resonance imaging (MRI) may be performed for the detection of cancer or cancer metastasis in patients determined to have a certain gut microbiome composition.

VI. Kits

Certain aspects of the present invention also concern kits containing compositions of the invention or compositions to implement methods of the invention. In some aspects, kits can be used to evaluate expression levels and/or the presence or absence of cell-surface markers. In certain aspects, a kit contains, contains at least or contains at most 1, 2, 3, 4, 5, 6, 7,8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules, detection agents, antibodies or inhibitors, or any value or range and combination derivable therein. In some aspects, there are kits for evaluating expression levels and/or cell surface expression of biomarkers in a cell.

Kits may comprise components, which may be individually packaged or placed in a container, such as a tube, bottle, vial, syringe, or other suitable container means.

Individual components may also be provided in a kit in concentrated amounts; in some aspects, a component is provided individually in the same concentration as it would be in a solution with other components. Concentrations of components may be provided as 1×, 2×, 5×, 10×, or 20× or more.

Kits for using probes, synthetic nucleic acids, nonsynthetic nucleic acids, and/or inhibitors of the disclosure for prognostic or diagnostic applications are included as part of the disclosure. Specifically contemplated are any such molecules corresponding to any biomarker identified herein, which includes nucleic acid primers/primer sets and probes that are identical to or complementary to all or part of a biomarker, which may include noncoding sequences of the biomarker, as well as coding sequences of the biomarker.

In certain aspects, negative and/or positive control nucleic acids, probes, and inhibitors are included in some kit aspects. In addition, a kit may include a sample that is a negative or positive control for biomarker expression levels.

It is contemplated that any method or composition described herein can be implemented with respect to any other method or composition described herein and that different aspects may be combined. The claims originally filed are contemplated to cover claims that are multiply dependent on any filed claim or combination of filed claims.

Aspects of the disclosure include kits for analysis of a pathological sample by assessing biomarker expression profile for a sample comprising, in suitable container means, two or more probes or detection agents, wherein the probes or detection agents detect one or more markers identified herein.

VII. EXAMPLES

The following examples are included to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific aspects which are disclosed and still obtain a like or similar result without departing from the spirit and scope of the invention.

Example 1: Treatment of Glioblastoma with KDM6B Inhibition

A subset of cancer patients treated with immune checkpoint blocade (ICB) therapies exhibit significant and durable anti-tumor responses. However, the responses vary across different tumor types. Tumor microenvironment plays a critical role in dictating the response to ICT. A recent analysis from the inventors' group evaluated tumor microenvironment of 5 different tumor types. The inventors noted that each tumor types have distinct tumor microenvironments (PMID: 31873309). While immune checkpoint therapy sensitive tumor types have higher infiltration of T lymphocytes, immune checkpoint resistant tumor types such as Glioblastoma (GBM) have almost no T cells in the microenvironment and mostly infiltrated by immune-suppressive myeloid cells. Notably, immune-suppressive myeloid cells persist in the GBM tumor microenvironment even after treatment with anti-PD-1 therapy (PMID: 31873309). Therefore, the inventors hypothesized that targeting the myeloid cells is critical for increasing the efficacy of ICB therapy.

Myeloid cells are a group of highly plastic cells, and myeloid plasticity is epigenetically regulated. EZH2, a histone methyltransferase, activates macrophages by suppressing SOCS3, a negative regulator of cytokine responses by trimethylation of H3K27 (PMID: 29626115). Therefore, macrophages devoid of EZH2 in a murine model have attenuated autoimmune encephalopathy. On the other hand, KDM6B, which is a demethylase of H3K27me can also bind to SOCS3 locus (PMID: 20729857). KDM6B has been shown to be important in M2 polarization. Based on these, the inventors tested if myeloid specific depletion of KDM6B can change the functional phenotype of myeloid cells in the context of GBM and if that can positively affect the anti-tumor immune responses in GBM.

Figure 2:
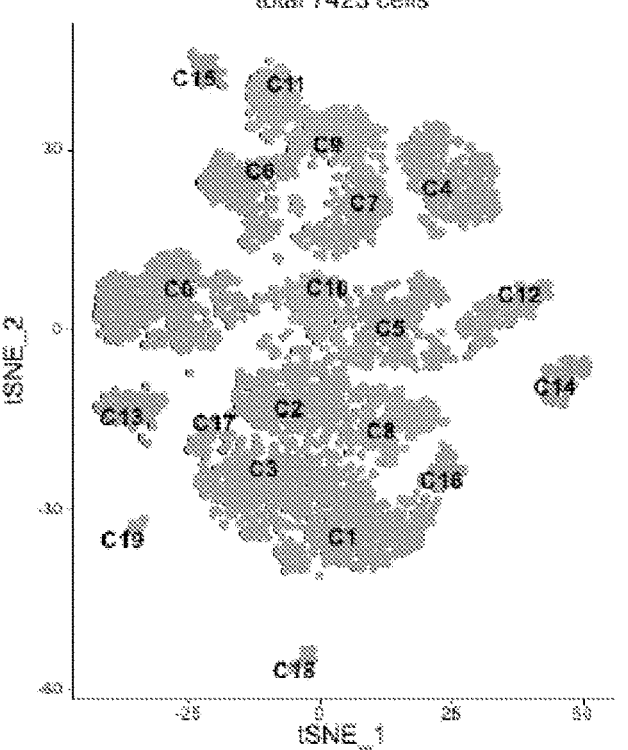
FIG. 2 shows myeloid specific depletion of KDM6B alters the immune microenvironment in GBM tumor bearing mice.
Figure 2:
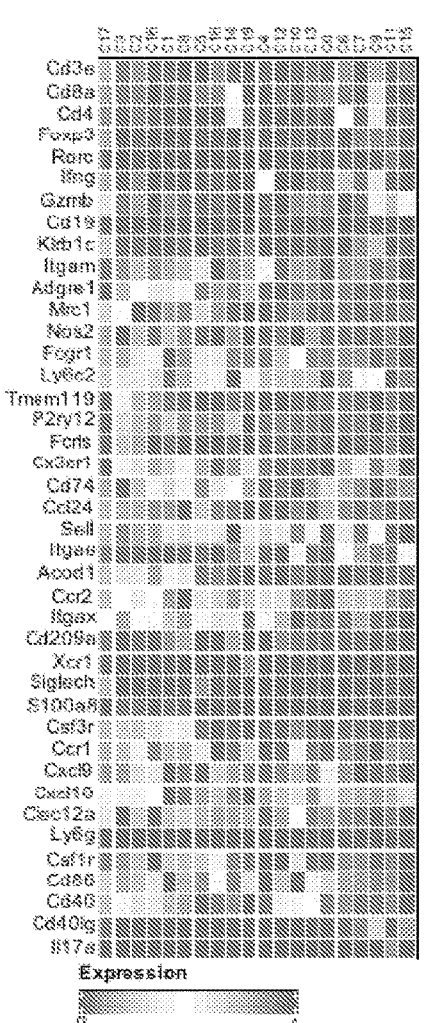
Figure 3:
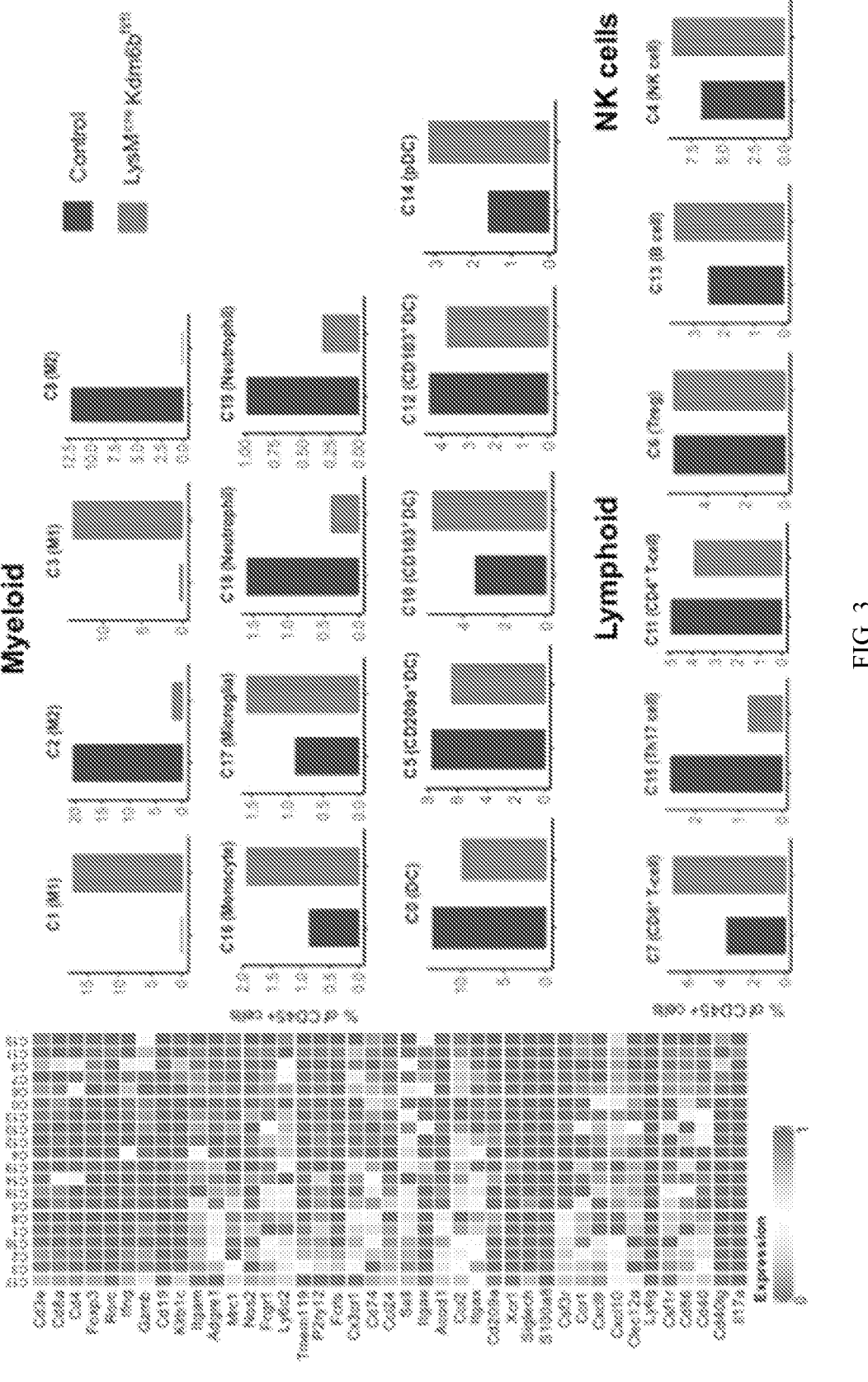
FIG. 3 shows myeloid specific depletion of KDM6B alters the immune microenvironment in GBM tumor bearing mice.
Figure 4:
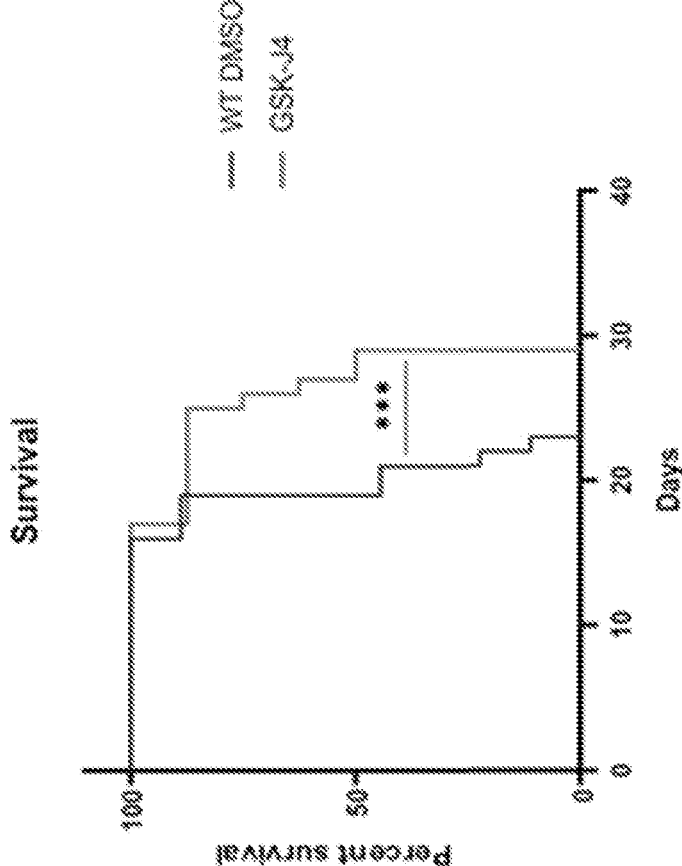
FIG. 4 shows that pharmacological inhibition of KDM6B attenuates tumor growth and improve survival of GBM tumor bearing mice.
Figure 4:
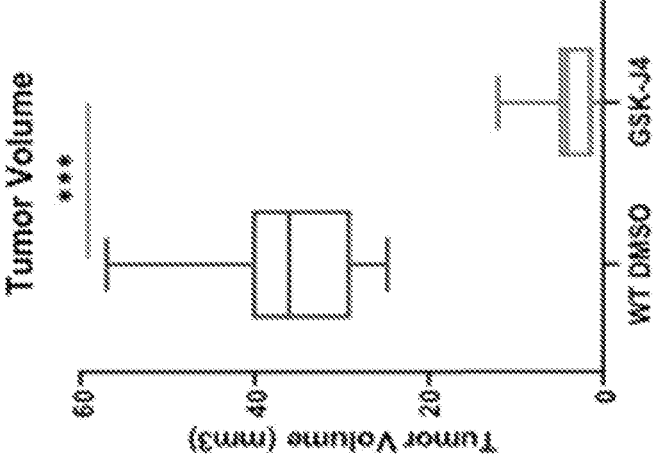
Figure 5:
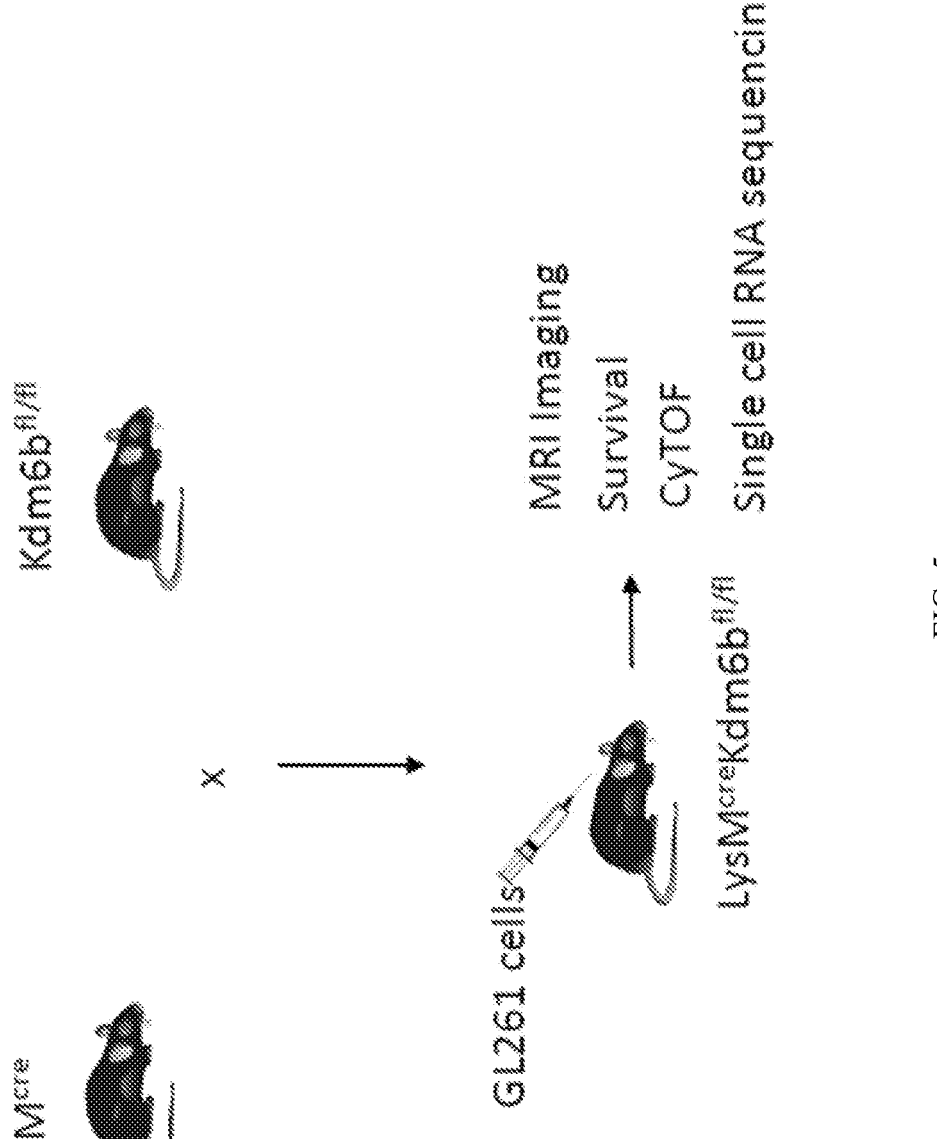
FIG. 5 is a schematic showing experimental details described in Example 1.
Figure 6A:
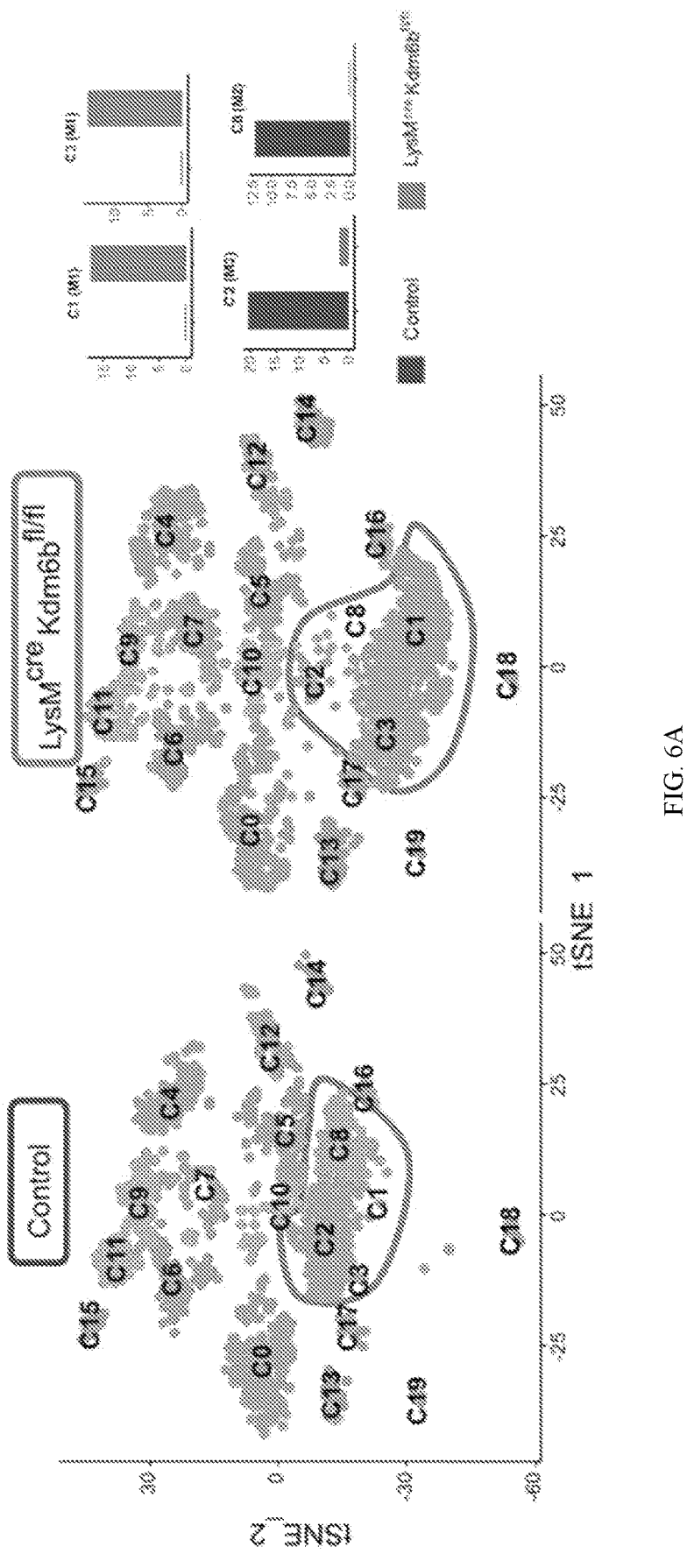
FIG. 6A-B shows that myeloid specific depletion of KDM6B increases antigenicity of myeloid cells.
Figure 6B:
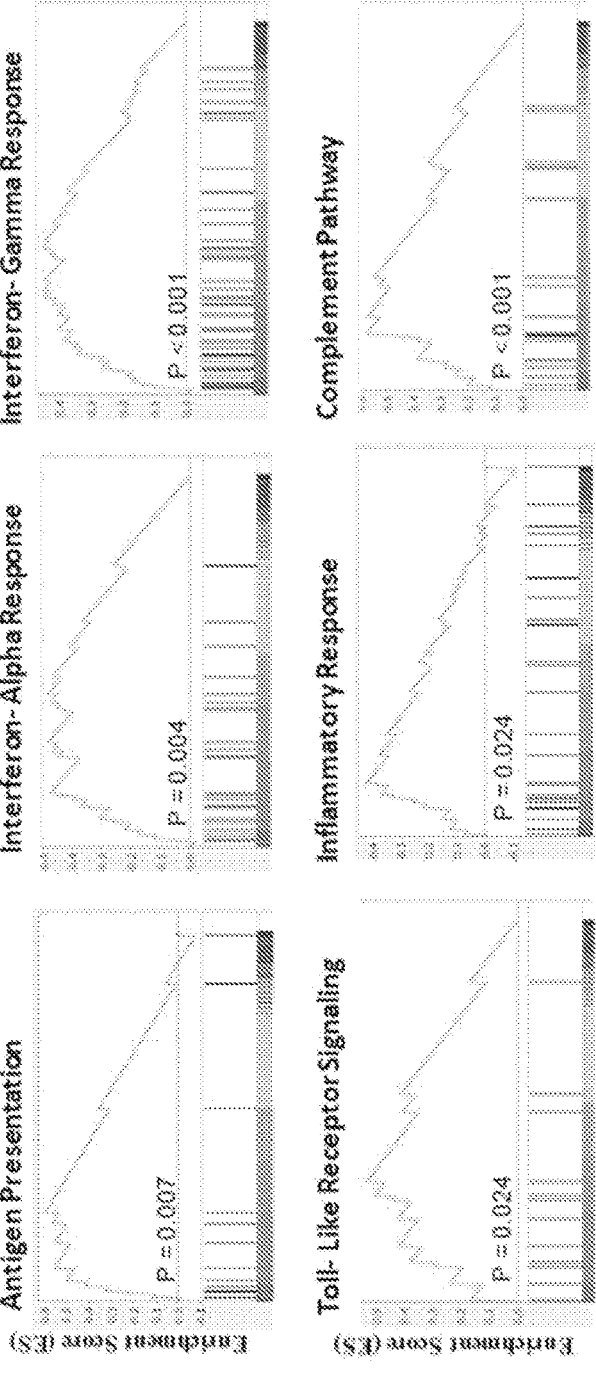
Figure 7:
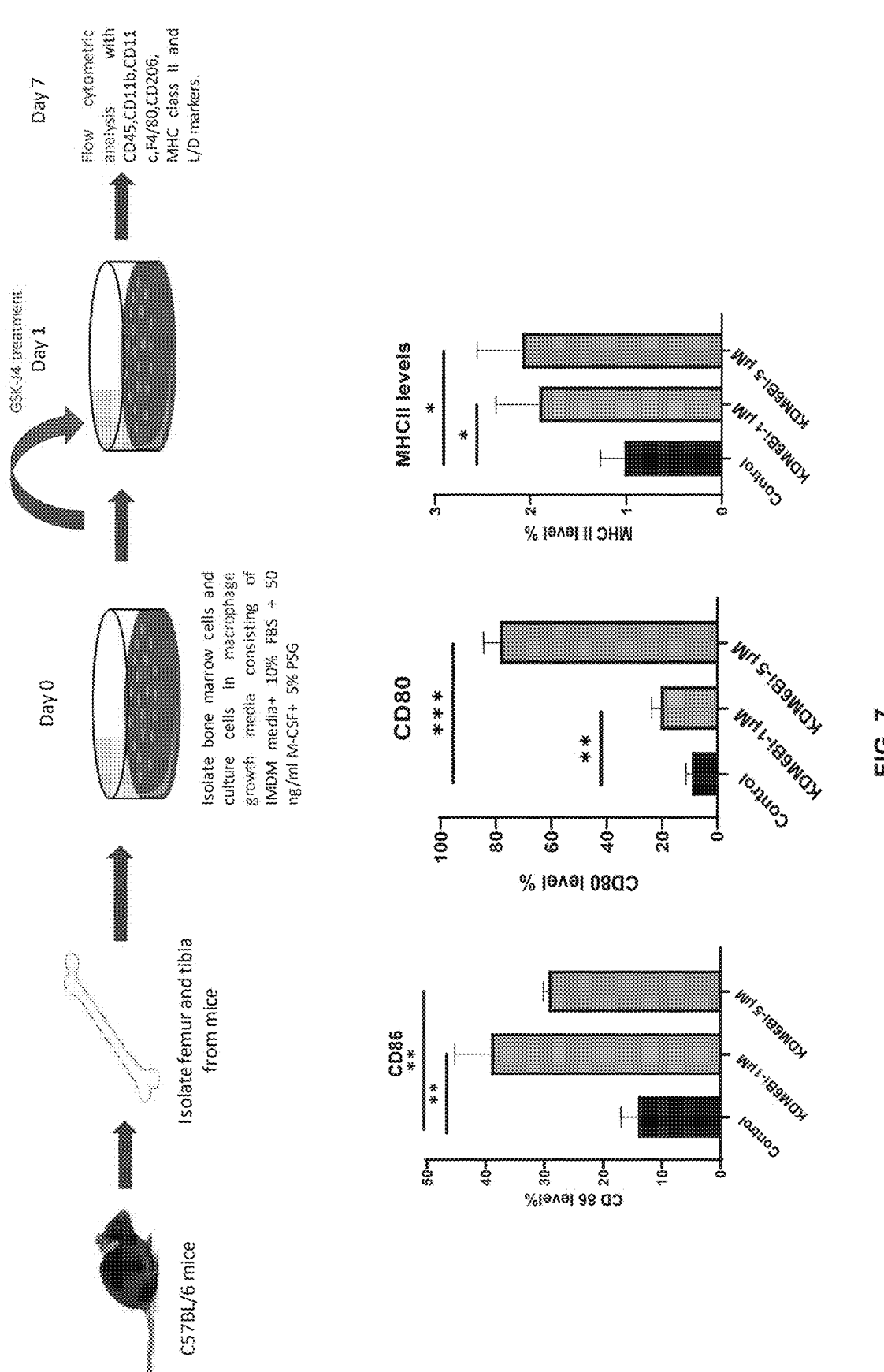
FIG. 7 shows that pharmacological inhibition of KDM6B increases antigenicity of myeloid cells.
Figure 8:
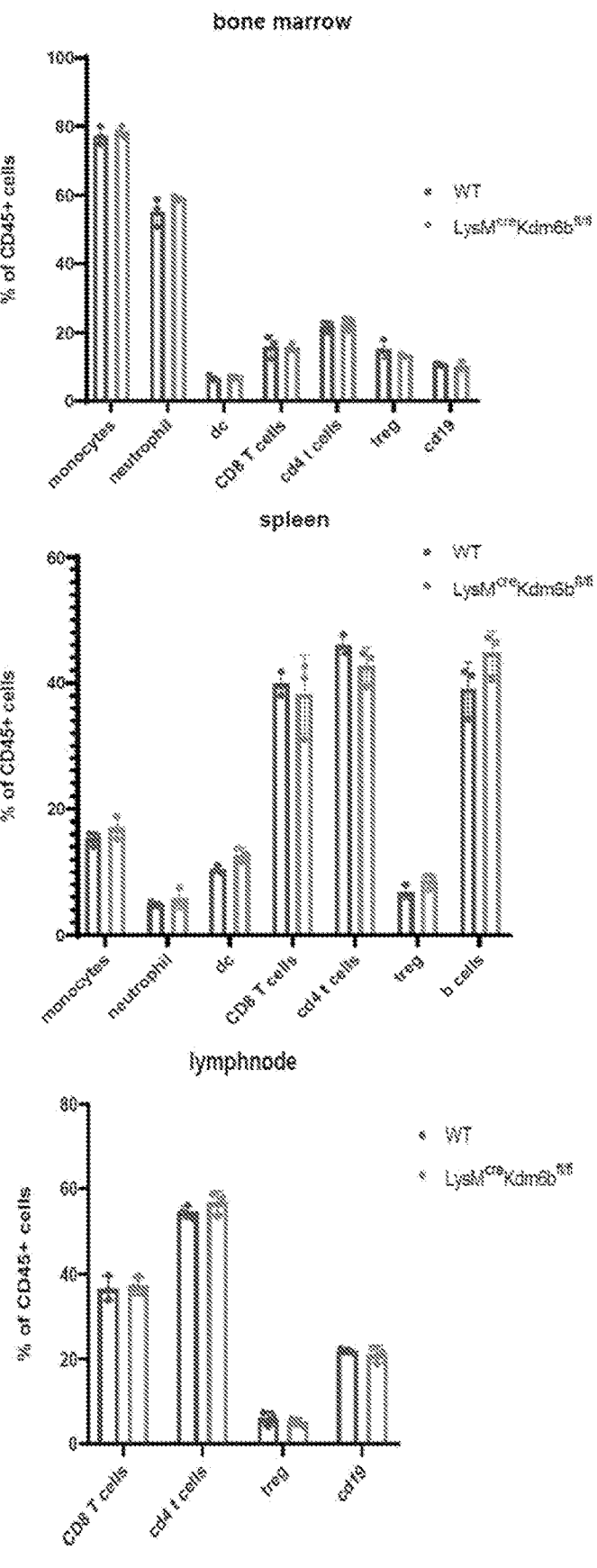
FIG. 8 shows the immunophenotyping of LysM$^{cre}$KDM6B$^{fl/fl}$ mice. Each set of 2 bars shows WT on the left and LysM$^{cre}$KDM6B$^{fl/fl}$ mice on the right.

To test this hypothesis, the inventors crossed LysM$^{cre}$ (Jackson Laboratory. 004781) and KDm6B$^{fl/fl}$ (Jackson Laboratory, 029615) mice to generate LysM$^{cre}$KDm6B$^{fl/fl}$ mice. The inventors inoculated murine GBM cell lines (GL261) into the LysM$^{cre}$KDm6B$^{fl/fl}$ mice (FIG. 5). The inventors showed that the deletion of KDM6B in myeloid cells significantly reduces tumor burden and improves survival of GBM tumor bearing mice (FIG. 1). Analysis of the tumor microenvironment demonstrated that the absence of KDM6B can change the phenotype of the macrophages with increasing type I and type II IFN responses and antigen presenting pathways (FIG. 2 and FIG. 3). Next, pharmacological inhibition of KDM6B (GSK-J4, catalogue number SML701) could recapitulate the changes of macrophage phenotype resulting in attenuated tumor growth and improved survival (FIG. 4). Together, this data showed that epigenetic modification of myeloid cells can attenuate tumor growth and might provide a permissive environment for ICT in GBM. The pre-clinical data provide a strong rationale of testing KDM6B inhibitor in clinic in combination with immune checkpoint therapy.

The appendix of the application provides further descriptive embodiments and further exemplifies the methods and compositions of the disclosure.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating refractory glioblastoma in a subject comprising administering to the subject a small molecule KDM6B inhibitor comprising GSK-J4 or a myeloid cell treated with the small molecule KDM6B inhibitor comprising GSK-J4, and an immunotherapy comprising an immune checkpoint blockade (ICB) therapy comprising anti-PD-1 or anti-PDL1 therapy.

2. The method of claim 1, wherein the glioblastoma is further defined as glioblastoma with myeloid infiltration.

3. The method of claim 1, wherein the myeloid cells are isolated from bone marrow cells from the subject or from a bone marrow donor.

4. The method of claim 1, wherein the ICB therapy comprises a monotherapy or a combination ICB therapy.

5. The method of claim 1, wherein the ICB therapy further comprises an inhibitor of PDL2, CTLA-4, B7-1, and/or B7-2.

6. The method of claim 5, wherein the ICB therapy further comprises an anti-CTLA-4 monoclonal antibody.

7. The method of claim 1, wherein the ICB therapy comprises one or more of nivolumab, pembrolizumab, pidilizumab, ipilimumab, and tremelimumab.

8. The method of claim 1, wherein the subject has been previously treated for glioblastoma with an anticancer agent.

9. The method of claim 8, wherein the previous treatment comprises an immunotherapy.

10. The method of claim 9, wherein the subject has been determined to be non-responsive to the previous therapy.

11. The method of claim 1, wherein the method further comprises administering at least one additional anticancer treatment.

12. The method of claim 11, wherein the small molecule KDM6B inhibitor, immunotherapy, and/or at least one additional anticancer agent is administered intravenously.

* * * * *